United States Patent [19]

Hata et al.

[11] 4,314,995

[45] Feb. 9, 1982

[54] PHARMACEUTICAL LACTOBACILLUS PREPARATIONS

[75] Inventors: Kosei Hata, Osaka; Tadayo Hata, Tondabayashi; Toshiyuki Maruoka, Toyonaka, all of Japan

[73] Assignee: Seikenkai, Osaka, Japan

[21] Appl. No.: 85,349

[22] Filed: Oct. 16, 1979

Related U.S. Application Data

[63] Continuation of Ser. No. 964,006, Nov. 27, 1978, abandoned, which is a continuation of Ser. No. 772,333, Feb. 25, 1977, abandoned.

[30] Foreign Application Priority Data

Feb. 23, 1976 [JP] Japan .................................. 51-19226

[51] Int. Cl.$^3$ .............................................. A61K 39/02
[52] U.S. Cl. ........................................ 424/93; 424/92
[58] Field of Search ................................... 424/92, 93

[56] References Cited

U.S. PATENT DOCUMENTS

| | | | |
|---|---|---|---|
| 1,729,752 | 10/1929 | Southgate | 424/93 X |
| 2,027,374 | 1/1936 | Fowler | 424/93 X |
| 2,944,941 | 7/1960 | Goldenberg | 424/58 X |
| 3,262,864 | 7/1966 | Kouchner | 424/93 X |
| 3,567,821 | 3/1971 | Nouvel | 424/93 |
| 3,639,566 | 2/1972 | Naito et al. | 424/93 X |
| 3,957,974 | 5/1976 | Hata | 424/93 |

FOREIGN PATENT DOCUMENTS

| | | | |
|---|---|---|---|
| 1185M | 3/1962 | France . | |
| 2946M | 11/1964 | France . | |
| 4430M | 9/1966 | France . | |
| 25675 | of 1910 | United Kingdom | 424/93 |

OTHER PUBLICATIONS

CA. 85 #166626p #197790a (1975) 83 #120838q (1975). 77 #168597p (1972) 75 #112871q (197). 73 #33916p (1970) 71 #53580M #53521n (1969). 70 #99628r (1969) 67 #89819c #102767 (1967). 66 #79593q (1967) 65 #75167d (1966) 63 #81341 (1965) 36 #3543 (4)(1942).

*Primary Examiner*—Shep K. Rose
*Attorney, Agent, or Firm*—Sughrue, Mion, Zinn, Macpeak & Seas

[57] ABSTRACT

This invention comprising a single or plural strains of Lactobacillus having special characteristics that have been never known is a new type of pharmaceutical Lactobacillus preparation for the treatment of infectious diseases.

Some of the characteristics of Lactobacillus used for the present invention as as follows.
(a) They are able to grow in low nutrition.
(b) The speed of multiplication is quick.
(c) By odoriferous S—, N— & C—compound, is promoted the growth.

The effects of the present invention are as follows.

Unlike the antibiotics which serves only to kill the bacteria, the present preparation is characteristic in that (a) it is non-pathogenic; (b) it can produce antibiotics thereby killing bacteria; (c) it can survive in the growth competition with pathogenic or other bacteria; (d) it denatures the metabolites (including poisonous ones) of living bodies or convert them into constituents of its own cells; (e) it purifies an affected part; (f) it shows anti-inflammatory or anti-swelling activities; and finally (g), as said preparation is foreign to the living bodies and is non-pathogenic, it is at least digested after the inflammatory diseases disappear. Accordingly, the present invention can be used extensively to give better therapeutic effects, except where the physical structure does not permit to use it.

43 Claims, No Drawings

PHARMACEUTICAL LACTOBACILLUS PREPARATIONS

This application is a continuation application of Ser. No. 964,006, filed Nov. 27, 1978, now abandoned in turn a continuation application of abandoned application Ser. No. 772,333, filed Feb. 25, 1977, abandoned.

This invention relates to a pharmaceutical preparation which comprises a single or plural strains of Lactobacillus as its active ingredient. More particularly, it relates to the lactobacillus preparation which is primarily useful for the treatment of infection or infectious diseases, i.e., one of the diseases which are hard to cure in the present day's medical science.

Intrusion of bacteria into living bodies and their proliferation are referred to as "infection". Once bacteria start proliferating in the living bodies or the latter start showing reactions (called as "infectious diseases") thereto, various symptoms may be observed such as fever, flare and swelling. The conditions of the infectious diseases may take a turn for the better when medicines such as antibiotics are used adequately at this stage. However, since the losing of a chance for the timely use of antibiotics, inadequate use thereof, discontinuing of the use thereof, drinking or other unexpected conducts, and further various phenomena (e.g., a phenomenon that the antibiotic does not reach enough to an affected part) may prevent the extermination or removal of bacteria from the infected living bodies, the medicinal treatment frequently proves unsuccessful. And in some cases the infectious disease may become chronic or be getting serious so that it will be difficult to be cured by the present day's medicinal science. The Lactobacillus preparation of the present invention (hereinafter referred to as "the present preparation") is especially effective for the treatment of these diseases.

Citing typical diseases such as nasal inflammation, gastritis or enterutis, alveolar brennorrhea, pudendal laceration and hemorrhoids which may be sometimes classified into incurable diseases, the use of the present preparation and examples of the medicinal treatment thereof are explained as follows.

(i) Nasal inflammation:

It is frequently observed that patients who catch cold and show nasal fluids discharge are, for some reasons, infected with pathogenic bacteria. Said bacteria proliferate profusely in nasal sinus and at last start producing toxins. The living bodies's reaction to the toxins causes inflammation which, though depending on its degree and kinds, induces the exudation of various substances. When the situation is getting serious, it may become extremely difficult to treat the disease because the nasal fluids is getting more mucous and antibiotics may not be able to penetrate such mucus or pus. Moreover, even the use of said antibiotics in combination with anitinflammatory enzymes would not have favorable effects to prevent the aggravation of the disease.

The above-mentioned facts indicate that in many cases the disease can not be cured by the use of antibiotics alone. Further, bacteria resistant to medicines appear under such situations and there are always brought about such secondary reactions that the disease is getting more chronic and serious. Excision is one of the medicinal treatment generally left in such situations. The adequate use of the present preparation (preferable in this case is the present preparation which is made of an antibiotic-producing strain) is effective irrespective of whether or not the treatment is carried out by the surgical means. Namely, when a large amount of the present preparation was applied to the inflammatory portion and repeatedly as the case may demand, bacterial substitution took place gradually and, depending on the conditions of patients, pathogenic bacteria apparently started losing their influence as early as the 2nd day or in about 15th day at the latest. Further, following the above, it was ascertained that the disease is gradually improved accompanying the abatement or disappearance of inflammation and swelling, dissolution or decrease of pus and purification of the focus of the disease. In this case, however, when compounds having bactericidal activity against Lactobacillus (e.g., horse radish, red pepper, curry) and medicines such as antibiotics intrude into nasal sinus, it sometimes happened that the condition of the disease takes a turn for the worse. This is primarily due to a fact that these bactericidal compounds prevent the proliferation of Lactobacillus. In such cases, therefore, it is especially important to use the present preparation which has been previously rendered resistant to the above-mentioned compounds.

In recent days, the combination of antibiotics and anti-inflammatory enzymes have been preferably used for the treatment of sinusitis and so forth. But even this newest methods may not be effective enough for the treatment of patients who show remarkable pus discharge, and surgical treatment may be usually required therefor. However, we have already observed many cases that even such serious disease could have been cured without surgical operation by the use of the present preparation.

(ii) Appendicitis:

Infection of pathogenic bacteria is one of the important causes of this disease. When having the trouble of appendicitis, pathogenic bacteria which induce inflammation gradually lack out into the upper- and lower-intestinal organs and usually remain there even after the operation for removing the appendix. In such infectious disease, the pathogenic bacteria distributed nearby survide there inveterately after the operation. Alternatively, it sometimes happens that patients are infected with bacteria in hospitals. In a sense, the above-mentioned infections are unavoidable and, though a large amount of antibiotics have been used generally for the treatment thereof, the use of said antibiotics still can not prevent the proliferation of pathogenic bacteria sufficiently. When the Lactobacillus strains of the present invention are employed in the above-mentioned situations, can bring about an early recovery from the disease because said strains can, as in the case of the inflammatory diseases, digest or denature the pathogenic bacteria (remained in the living bodies after the operation) and cell's or serum's secretion or exudate (produced by the biophylaxis reaction). Anyway, as antibiotics may be frequently used under these situations, the Lactobacillus strains to be used should be the one which is resistant to bactericidal agents.

(iii) Gastritis and enteritis:

Though even in these days it may not be rare that patients having poor resistability to these diseases (e.g., the infants and the aged) are died of marasmus, pathogenic bactera-induced gastritis and enteritis as well as the inflammatory diseases caused by bacteria such as enteritis vibrio, dysentery bacteria or salmonella may be normally gradually improved in a few days by the adequate use of antibiotics. However, some of these pathogenic bacteria may be resistant to the antibiotics used. In the latter cases, the diseases may not be improved by the use of antibiotics alone, but may be becoming more chronic or further induce secondary diseases frequently. In the medicinal fields, therefore, it is of greatest importance to cure the diseases before they become chronic. For this purpose, it is desirable to administer to the patients a large amount of the present preparation, if required, in combination with antibiotics. Moreover, even in the cases where the diseases may be improved in a few days by administration of a suitable drug, the use of the present preparation is recommended because it can bring about an earlier recovery from the disease and at the same time sweep away all the causes thereof.

(iv) Sputum:

Sputum is, like pus, formed by the pathological reaction of living bodies. In addition, sputum itself stimulates the living bodies to further form sputum, and the formation of sputum continues endlessly when the conditons of the disease is getting worse. The phenomenon is fundamentally the same as in case of sinusitis. Even in this case, the Lactobacillus strains of the present invention can purify the sputum because, as observed in the intestine, the digest, decompose or denature the nutrients contained in the sputum.

(v) Gingivitis:

When the inflammatory portion of living bodies are treated with, for example, antibiotics and anti-inflammatory enzymes, said treatment frequently results in poor success and bacteria still remain alive without being dispeled by the antibiotics, anti-inflammatory enzymes and the biophylaxis reaction of the living bodies. Said phenomenon is observed most frequently in, for example, alveolar abscess. This is, in addition to the insufficient therapeutic effects of the drugs, primarily due to a fact that gum tissues have not yet been restored completely at the time the pathogenic bacteria's cellular amount decreased significantly.

In such cases, the bacteria which remain in the oral cavity, the gap in the teeth and gums restore their vitality again to have the patients relapsed into the intitial bad conditions. When the amount of pathogenic bacteria is decreased in this type of diseases, therefore, it is important to administer the present preparation. By the administration of the present preparation, the quantitative ratio of the remaining pathogenic bacteria to the Lactobacillus strains of the present invention are reversed and, simultaneously, the conditions or color of the gums which showed the inflammation and swelling may be improved significantly.

Namely, when the local section infected must be treated urgently, antibiotics may be employed to kill pathogenic and non-pathogenic bacteria. And thereafter the inflammation caused by the biophylaxis reaction can be preferably improved by the use of the present preparation having potent purification ability.

(vi) Hemorrhoids:

Though quite various interpretations about the causes had been proposed in the past, relatively unified views about said causes have been set forth in recent days.

The first one of said causes has close relationships with the infection of pathogenic bacteria, i.e., the kinds and quantity of the pathogenic bacteria; and the second causes has something to do with intenstinal bacteria, i.e., fecal infections; the third to the structure of intestinal organs or anus; the fourth to the degree and frequency of irritation upon the local section, i.e., constipation and solidity of excrements; the fifth to the mode of living bodie's reaction (i.e., the conditions of the wound) and the recuperative ability on that portion (i.e., the physical constitution); and the sixth to the degree and scope of blood congestion. When reviewing the above again (i.e., the wound, laceration and bacterial infection which are peculiar to the hemorrhoids), it may be rare that patients are afflicted, on account of laceration alone, with serious hemorrhoids which affects their daily life. Namely, the hemorrhoids can be considered as the inflammation of the anus and its surrounding portions which are caused primarily by bacterial infection or by combination thereof with various other causes. Further, the condition and degree of of the disease may vary depending on the bacteria, the interrelation with intestinal bacteria, the reactivity of living bodies, the degree of irritation or the place of the affected part. Therefore, it may not always be suitable to discuss said disease comprehensively at the same level. In this connection, however, it is an undeniable fact that in almost all cases bacterial infection is playing an important role for this desease. In this sense, therefore, it should be recognized that various symptoms of hemorrhoids is indicating various aspects of bacterial infection. And based on this understanding, the hemorrhoids should be considered, like laryngitis or various inflammation caused by birth canal's laceration, as the most complicated and unclassable typical model of inflammation which is primarily caused by bacterial infection.

As stated above, the hemorrhoids is one of the most incurable diseases and, in the case of this disease, the difficult is ascertaining the kinds of pathogenic bacteria, the resistance thereof to drug, the degree of local osmosis of the pathogenic bacteria and infectiosity thereof render even the choice of drugs quite difficult.

Further, whether a drug is in fact effective for the intestinal bacteria in the body of the patients must be decided independently of the bactericidal activity of the drug because it is unavoidable for patients to be infected with a huge amount of various intestinal bacteria. These two points make the choice of suitable drugs more difficult.

Additionally, although many proposals based on the therapeutic experiments have been made for the treatment of the disease, human beings will undoubtedly be afflicted with this disease over a long period because the hemorrhoids of many kinds involve intricate causes. In this respect, however, the use of the present preparation brings us a bright future and enables the therapy of the hemorrhoids to make a step forward.

In summing up: First of all, the specific Lactobacillus strains which are used in the present invention have a characteristic ability to control or prevent the growth of other living microorganisms. This fact was proven during the investigation for deodorizing excrements. This ability also serves to prevent the growth of, to kill, or to induce bacterial substitution of, the pathogenic bacteria which form the focus of disease in the local section. Moreover, said ability works effectively against intenstinal bacteria, too. Futher, since the Lactobacillus strains of the present invention kill the bacteria found on and around the inflammatory portion or show a protective effect against intestinal bacteria, and also since the balance of power between the Lactobacillus and the intestinal bacteria is changed in favor of the former thereby decreasing the amount of putretative bacteria in the intestine, the above-mentioned ability of the Lactobacillus strains can lighten the burden which the living bodies must bear for the purpose of phylaxis. In addition, the strong purifying ability of the present preparation has already been proven through the experiments concerning the deodorization of stinking materials.

Further, the strains used in preparing the present preparation include those having strong antibiotic-productivity. In such cases, the present preparation exerts much more potent ability to prevent the growth of pathogenic or non-pathogenic bacteria and, as a result, the conditions of the hemorrhoids can be frequently improved, or if not serious, cured almost completely by the use of the present preparation.

As is clear from the analysis as to the phylaxis, among the inflammatory diseases of living bodies this group of disease is characteristic in the strong irritation and the contamination of the affected part. Thus, disease which affect so adversely upon the hose as in the case of the hemorrhoids, may be relatively rare. In other words, such serious disease may be found only in the infected eyes, oral cavity, gums, throat, abdominal cavity or sexual organs, or in the operated patients in the field of the gynecology.

Concomitantly, although in the foregoing description only the pathogenic bacteria was explained as responsible for the hemorrhoids and it was distinguished from intestinal bacteria, it should be noted that said disease are sometimes induced by intestinal pathogenic bacteria.

(vii) Pudendal laceration at the time of child-birth:

Oral administration of the present preparation or the direct application thereof to the affected part are useful to improve the inflammatory symptoms including swelling, flare or pain in the local section.

We carried out experiment using the Lactobacillus strains which are resistant or not resistant to drugs or popular condiments. In order to make the present preparation exert its effects sufficiently, it had to be first ascertained that the inflammation of the living bodies were disappeared completely. However, since chronic inflammatory diseases can not be cured within a short period, it is impossible in the present day's food life to continue a living without taking any condiments until the complete recovery from the disease. For this reason, therefore, in making the pharmaceutical preparation of the present invention it is important to use the Lactobacillus strains which are resistant to condiments or antibiotics.

The experiments were carried out extensively, and herein described is only a part of such experiments.

Since the development of bactericidal agents and antibiotics including red prontosil and penicillins, these products have been used extensively for the treatment of bacteria-induced diseases, because they not only involved new inventive concepts but also had potent bactericidal activity with less detrimental effects upon living bodies. The present preparation has the novelty, high effectiveness and wide applicability which are almost comparable to those of sulfa agents, antibiotics and anti-inflammatory enzymes.

Naturally, the present invention is characteristic in that, when administered orally, it can decrease the peculiar odor of excrements at the time of their excavation. That is, even in the intestine covered with more than $10^{11}$ cells/g of microbes forming their own peculiar mass of spores, the present preparation can proliferate well and predominates over said microbes. This is because the Lactobacillus strains of the present invention can grow faster than almost all intestinal bacteria; require less nutrients; can simultaneously produce antibiotics; and therefor can survive in the growth competition with intestinal bacteria. The stinking materials in the excrements involve many kinds of compounds such as various amines, lower fatty acids, ammonia and sulfur compounds. When the amount of these materials exceeds over some limit, they become poisonous to living bodies. The deodorizing effect of the present preparation for these materials clearly indicates that it can digest or denature these materials thereby decreasing the amount of the latter or converting them to other materials. Moreover, these effects of the present preparation are obtained in the presence of a large amount of intestinal bacteria which produce the stinking materials, while preventing the growth of the latter. Accordingly, said effect is one of the most important point of the present invention, and said characteristic effect or ability is displayed quite satisfactorily even in other affected parts of infectious diseases. Further, since the Lactobacillus strains of the present invention (which utilize as their nutrients the cells or exudate floated out in the living bodies) can grow very rapidly, the substitution thereof for other bacteria can proceed without being interfered with the latter.

Some examples of the medicinal treatment mentioned above indicate that the Lactobacillus strains of the present invention can predominate over the pathogenic bacteria in the growth competition thereof with said bacteria. Further, the purification action of the present preparation has already been proven through the experiments of deodorization (Deodorization is one indication of the purification action). Thus, the Lactobacillus strains can temporarily proliferate profusely, but its growth may be minimized as the nutrient sources thereof (i.e., the exudate from the inflammatory portion) disappear In summing up the effects of the present preparation: unlike the antibiotics which serve only to kill the bacteria, the present preparation is characteristic in that (a) it is non-pathogenic; (b) it can produce antibiotics thereby killing bacteria; (c) it can survive in the growth competition with pathogenic or other bacteria; (d) it denatures the metabolites (including poisonous ones) of living bodies or convert them into constituents of its own cells, (e) it purifies an affected part; (f) it shows anti-inflammatory or anti-swelling activities; and finally (g), as said preparation is foreign to the living bodies and is non-pathogenic, it is at least digested after the inflammatory diseases disappear. Accordingly, as is clear from the aforementioned discussions about the causes of the diseases or from the experimental data thereof, the present preparation can be used extensively to give better therapeutic effects, except where the physical structure does not permit to use it.

Moreover, we have ascertained that these therapeutic effects of the present preparation are sometimes increased when used in combination with enzymes having anti-inflammatory, anti-swelling or abating activities. Namely, although it is impossible to sweep away microbes by the use of the enzymes having such activities, and although antibiotics show only the alleviation of the swelling induced by the inflammatory diseases or have insufficient effects thereon, the diseases can be frequently improved very significantly by the use of the present preparation because of the bacterial substitution taken place.

Turning now to the non-pathogenic property of the strains used in the present invention. Originally, the history of bacteriology began with Pasteur's study about lactic acid bacteria. Despite a fact that too many investigations about Lactobacillus have been carried out since 1857, it has been said that any scientific reports have not proven positively this group of strains to be pathogenic. Moreover, not only the dissertations reliable in these days show the Lactobacillus to be non-pathogenic, but Bergey's Manual (1974) also discloses specifically that pathogenic bacteria belonging to said group are extremely rare.

According to the inventor's investigations, it has been proven that the Lactobacillus is almost essential to the living bodies, i.e., to mucous membrane, and especially essential at least in the oral cavity, intestine and vagina. For example, it is almost impossible to maintain the normal conditions of the vagina if the Lactobacillus is not present therein. Therefore, whether the Lactobacillus is present or not has recently been an important check-point in making a diagnosis of the health condition of the vagina.

Meanwhile, although the strains which are used in the present invention apparently belong to the group of Lactobacillus, whether or not said strains of the invention is pathogenic has not yet been known up to now because they have some properties not known heretofore.

The fundamental problem to be determined first is whether or not the new strains of the present invention belong in fact to the Lactobacillus. If they belong to the Lactobacillus without doubt, this fact alone will indicate with a very high possibility that they are non-pathogenic.

All the morphological properties of the new strains isolated herein are, except for the nutrieitional requirements, identical with those of the known strains of Lactobacillus. The Lactobacillus strains known heretobefore can be defined as gram-positive, facultative anaerobes and non spore-forming rods. The shape of them vary depending on the strains from spherical rod-like to curved rod-like, coryne-like or thread-like, but they do not form so many branches. They are usually non-mitile, negative to catalase, do not reduce nitrates, do not decompose gelatin and do not form indole or $H_2S$. Some strains are bipolar-stained. The ability of the Lactobacillus strains to decompose proteins and lipase is very poor, if any. They show better growth under aerophobic or slightly aerophobic conditions than under aerophilic conditions. They decompose sugar strongly and are acid-fast bacteria. Lactic acid is produced in an yield of more than 50% by the glucose fermentation thereof. According to the known morphological classification, the strains of the present invention having these properties should be construed to belong to the group of lactobacillus. Moreover, the morphology of microorganisms has not provided a clue to classify microbes according to the difference in the nutritional requirements thereof. At least at present, therefore, it is considered that the strains of the present invention below to the Lactobacillus. Concomitantly, assuming that some different classification method would be adopted in future to classify these strains to a different group, the strains of the present invention would have to be classified into a group which is quite similar to the group of Lactobacillus. A fact that the strains of the present invention are classified into the group of Lactobacillus or its quite similar group is of special importance in discussing the non-pathogenic property thereof.

The reason why we selected Lactobacillus in seeking deodorizing microbes for oral administration, despite a fact that other bacteria such as the strains of Pseudomonas were thought to be available more easily, was that it was thought this group of microbes should be understood as useful strains. Especially, as one of important members of intestinal bacteria, It was thought that they should be recognized to be most important and essential to the intestine. In fact, although at the initial stage of experiments it was highly worried that the deodorizing microorganisms isolated as desired might, when administered orally, give a bad influence to the regular evacuation and other daily life, it was just this view-point about the non-pathogenic property and usefulness thereof that could drive us to continue various experiments.

First of all, we carried out experiments using various dogs. Then, at the final state of the experiments the washed culture clots (wet 0.1 g/kg) was administered to both human subjects and dogs almost every consequtive days or sometimes at the intervals of 2 or 3 days for 2 years. But no pathogenic effects were observed during the experiments, and the human subjects tested showed a decrease of fatigue and improvement of their health conditions as their subjective symptoms. Moreover, 2 dogs which were always under the care of veterinarians recovered their health and came to continue their life without the care of veterinarians.

Accordingly, the strains of the present invention when administered orally to human beings show neither acute, subacute nor chronic toxicity. Moreover, when one mg/g of said strain suspended in 3-fold volume of a physiological saline solution was injected intraperitoneally to 50 mice, as compared with a control group the tested mice did not show any irregular symptoms 24, 48 or 72 hours, one week, one month or 3 months after the administration. Namely, the above-mentioned facts indicate that the strains of the present invention may not show any acute or sub-acute toxicity even by administering 60 g of the clots of the microbial cells to human beings of 60 kg body weight. Therefore, the present preparation is considered to be substantially free from pathogenic property.

Next, the properties of the Lactobacillus strains of the present invention isolated and cultivated herein, and the method of preparation thereof, are shown with full particulars in the following lines.

(a) Bile resistance:

In order for the Lactobacillus strains to show their activity sufficiently in the intestines, it is essential that said strains are resistant to bile or have an affinity therefor.

The bile resistance of the typical strain 1946/F.R.I. used in the present preparation is shown in Table 1.

Other typical strains of the Lactobacillus, i.e, 2779/F.R.I., 2780/F.R.I., 2781/F.R.I. and 2782/F.R.I., which were isolated successfully by the inventors and usable in the present invention showed almost the same properties against bile as in the case of 1946/F.R.I. That is, they could proliferate well in a medium containing 4 by weight % of bile extracts. Of course, the present preparation which is not resistant to bile may, dependent on places to be applied, also show its effects sufficiently.

TABLE 1

| Medium | Bile extracts | | | | |
|---|---|---|---|---|---|
| | 0% | 1% | 2% | 3% | 4% |
| S-W medium + casamino acids | + | *<br>+⊥ | *<br>+⊥ | ++ | + |
| S-W medium + Na₂S | + | *<br>+⊥ | *<br>+⊥ | ++ | + |
| Meat extract bouillion | + | *<br>+⊥ | *<br>+⊥ | *<br>+⊥ | + |

Note:
+, ++ and +⊥ show the degree of growth
+ : good growth
++ : further good growth
+⊥ : intermediate growth of + and ++
Components of S-W medium KH₂PO₄ 1 g, MgSO₄ . 7H₂O 0.7 g, NaCl 1 g, (NH₄)₂HPO₄ 4 g, FeSO₄ . 7H₂O 0.03 g and glucose 5 g.

(b) Nutritional requirements:

Unlike the known strains of Lactobacillus which require amino acids, peptides, nucleic acids, vitamines, salts, fatty acids or their esters and sugars for their growth, the lactobacillus strains of the present invention show less nutritional requirements. Nevertheless, they show good growth within a short period of time such as 2 days and form lactic acid. Table 2 shows the degree of growth thereof in each media. S-W medium and S-W+Agar medium were used as the basic media therein.

TABLE 2

| Compounds added to the basic medium | Basic medium | Strains (F.R.I. Nos.) | | | | |
|---|---|---|---|---|---|---|
| | | 1946 | 2779 | 2780 | 2781 | 2782 |
| No addition | (A) | − | − | − | − | − |
| | (B) | − | − | − | − | − |
| Sulfur-containing amino acids | (A) | + | − | − | + | − |
| | (B) | ++ | − | ⊥ | + | − |
| Cyclic amino acids | (A) | ⊥ | − | − | − | − |
| | (B) | ⊥ | − | − | ⊥ | − |
| Branched amino acids | (A) | − | − | − | − | − |
| | (B) | − | − | − | ⊥ | − |
| Cystein | (A) | + | − | − | ⊥ | − |
| | (B) | ++ | − | − | + | − |
| Cystine | (A) | + | − | − | ⊥ | − |
| | (B) | ++ | − | − | + | − |
| Methionine | (A) | + | − | − | ⊥ | − |
| | (B) | + | − | − | + | − |
| Casamino acids | (A) | + | ⊥ | ⊥ | + | ⊥ |
| | (B) | ++ | + | + | + | + |
| Casamino acids + Vitamines | (A) | + | + | + | + | + |
| | (B) | ++ | + | + | ++ | + |
| Casamino acids + yeast extracts | (A) | +⊥ | + | + | + | + |
| | (B) | ++ | + | + | ++ | + |
| Yeast extracts | (A) | + | + | + | + | + |
| | (B) | ++ | + | + | ++ | + |

Note:
(A) : S-W medium
(B) S-W medium (+ Agar)
+ : Normal growth
++ : Good growth
+++ : Very good growth
⊥ : Poor growth
− : No growth (c) Specific growth rate:

As seen in Table 3, the Lactobacillus strains of the present invention show surprisingly high specific growth rate even in innutritious media. Just for comparison, the specific growth rate of Escherichia coli are shown in the table.

TABLE 3

(Basic medium: S-W medium)

| Strain Nos. F.R.I. | Ingredients added to the basic medium | S,N,C and sulfur-containing amino acids | μ | μ in case of Escherichia coli |
|---|---|---|---|---|
| 1946 | Sulfur-containing amino acids | Yes | 0.53 | 0.4 |
| 2779 | Vitamines, sulfur-containing amino acids | Yes | 0.46 | 0.43 |
| 2780 | Vitamines | Yes | 0.46 | 0.38 |
| 2781 | S,N,C | Yes | 0.53 | 0.35 |
| 2782 | Vitamines, sulfur-containing amino acids | Yes | 0.46 | 0.43 |

Note:
S : S-compounds Na₂S or N₂S
N : N-compounds ammonia, indole or scatole
C : C-compounds lower fatty acids (acetic acid, butyric acid and the like)
Yes : essential for growth Namely, although the known strains of Lactobacillus show high nutritional requirements and lower growth rate as compared with pathogenic bacteria, the Lactobacillus strains of the present invention can predominate over the generally known pathogenic bacteria in the growth competition therewith.

(d) The results of microscopic observation and the morphological characteristics of the Lactobacillus strains of the present invention are shown in Table 4. Tables 5 and 6 show the biochemical properties and the ability to decompose sugars, respectively.

TABLE 4

Microscopic observation and morphological characteristics

| | F.R.I. Nos. | | | | |
|---|---|---|---|---|---|
| | 2779 | 2780 | 2781 | 2782 | 1946 |
| Gram | + | + | + | + | + |
| Shape | short rod, rounded ends, no flagella and no spore | coccobacilli, no flagella and no spore | coccobacilli, no flagella and no spore | short rod, rounded ends, no flagella and no spore | short rod, rounded ends, no flagella and no spore |
| Capsule | No | No | No | No | No |
| Motility | No | No | No | No | No |
| In a medium | anaerobic round | anaerobic round | anaerobic round | anaerobic round | anaerobic round |

TABLE 4-continued

| | Microscopic observation and morphological characteristics | | | | |
|---|---|---|---|---|---|
| | F.R.I. Nos. | | | | |
| | 2779 | 2780 | 2781 | 2782 | 1946 |
| of (Agar + sugar + vitamines) | middle colonies | middle colonies | middle colonies | middle colonies | middle colonies |
| Projection | Semi-spherical | Semi-spherical | Thin | Thick | Thick |
| Surface | smooth moistened | smooth moistened | smooth moistened | smooth moistened | smooth moistened |
| Circumference | Plain | plain | plain | plain | plain |
| Color | milky white, not transparent, mucous | milky white, not transparent, mucous | white, not transparent, mucous | milky white, not transparent, mucous | milky white, not transparent, mucous |

TABLE 5

| (General properties) | | | | | |
|---|---|---|---|---|---|
| | F.R.I. Nos. | | | | |
| | 2779 | 2780 | 2781 | 2782 | 1946 |
| Ammonia-production | − | − | − | − | − |
| H₂S-production | − | − | − | − | − |
| Catalase-production | − | − | − | − | − |
| Pigment-production | − | − | − | − | − |
| Gelatin liquefaction | − | − | − | − | − |
| Utilization of citric acid | − | − | − | − | − |
| Decomposition of urea | − | − | − | − | − |
| M.R. reaction | + | + | + | + | + |
| V.P. reaction | − | − | − | − | − |
| Reduction of nitrates | − | − | − | − | − |

TABLE 6

| (Ability to decompose sugars) | | | | | |
|---|---|---|---|---|---|
| | F.R.I. Nos. | | | | |
| | 2779 | 2780 | 2781 | 2782 | 1946 |
| Glucose | + | + | + | + | + |
| Galactose | + | + | + | + | + |
| Fructose | + | + | + | + | − |
| Salicin | + | + | + | + | − |
| Arabinose | − | + | − | − | − |
| Xylose | − | − | − | + | − |
| Sucrose | + | + | + | + | + |
| Inositol | − | − | − | − | − |
| Dextrin | + | + | ± | ± | − |
| Mannitol | − | − | − | − | − |
| Melebiose | + | + | + | + | + |
| Ribose | + | + | + | + | − |
| Lactose | + | + | + | + | + |
| Raffinose | − | − | + | + | − |
| Starch | + | + | + | + | + |
| Inuline | − | − | − | − | − |
| Sorbitol | − | − | − | + | − |
| Maltose | + | + | + | + | + |
| Melezitose | − | − | − | − | − |
| Mannose | + | ± | + | + | − |

Antibiotic-productivity:

Although some strains belonging to the Lactobacillus have been known to show an antibiotic-productivity, all the strains of the present invention have this antibiotic-productivity. Said productivity of the Lactobacillus strains of the present invention serves to prevent the growth of other bacteria or the formation of pus, sputum, serum and other poisonous materials and can increase their various physiological activities.

Table 7 shows one example of the inhibitory effects against bacteria which were estimated by placing a trace of the Lactobacillus strains of the present invention at the center of a petri dish containing (agar+-sugar+vitamines)-medium, cultivating it at 37° C. for 2 days, and then spreading Staphylococcus aureus (as a representative example of gram-positive bacteria) or Escherichia coli (as a representative example of gram-negative bacteria) on the medium. In actual cases, however, depending on the components of the media and the methods of cultivation or storage it may sometimes happen that the strains of the present invention show the antibiotic-productivity stronger than those indicated in Table 7 or do not show any antibiotic-productivity.

TABLE 7

| Strains | Bactericidal activity Inhibition diameter (pre-cultivated for 48 hours) | |
|---|---|---|
| (F.R.I. Nos.) | Staphylococcus aureus | Escherichia coli |
| 1946 | 20 mm | 24 mm |
| 2772 | 15 mm | 18 mm |
| 2780 | 15 mm | 20 mm |
| 2781 | 12 mm | 15 mm |
| 2882 | 18 mm | 22 mm |

(f) Table 8 shows that the Lactobacillus strains used in the present invention are, though varying with the basic media employed, promoted their growth by adding various odoriferous ingredients of excrements to the media. Additionally, similar results were obtained by adding S, N, C-substances other than those shown in said table.

Then, the general summary of the fundamental bacteriological differences between the known Lactobacillus strains and those of the present invention are shown in Table 9-(a), Table 9-(b) and Table 9-(c). First of all, the relation between the growth and nutrition of known Lactobacillus strains and those of the present invention under low, middle or high nutritional conditions are shown at left side in Table 9-(a) and the degree of stimulation by adding acetic acid in their growth are shown at right side in the same table. This table indicates the clear difference between said both groups. Namely, although the addition of a suitable amount of acetic acid to a good nutritional medium (e.g., Briggs's medium which is typical one for the Lactobacillus) has been known to promote the growth of the known strains of Lacobacillus, such phenmenon can be observed only in good nutritional media. In other words, since the known Lactobacillus strains can not grow in a low nutritional medium, the addition of acetic acid never serves to stimulate the growth thereof. On the contrary, the Lacto bacillus strains of the present invention are promoted their growth strongly by adding a suitable amount of acetic acid to the low or relatively low nutritional media shown in Table 9-(a); but in the good or relatively good nutritional media, the higher are the nutritions added, the lower are received the stimuli quickly by them.

Moreover, as seen in Table 9-(b), when the known Lactobacillus strains and those of the present invention are cultivated in the low, middle or high nutritional media containing $Na_2S.9H_2O$ and $NH_3$, the growth of the strains of the present invention in the low or middle nutritional media is stimulated by addition of 0.1 g or 1 g of $Na_2S.9H_2O$, whereas said addition to the low, middle or high nutritional media does not stimulate the growth of the known lactobacillus strains.

Further, the growth of the Lactobacillus strains of the present invention in the low or middle nutritional media is stimulated by the addition of $NH_3$.

Thus, it is clear that, unlike the known strains, the Lactobacillus strains of the present invention show new and special behaviors to $Na_2S$ and ammonia under certain nutritional conditions.

Furthermore, the growth of the Lactobacillus strains of the present invention in the low, middle or high nutritional media are stimulated by addition of a mixture of $Na_2S.9H_2O$, ammonia and acetic acid, whereas the addition of said mixture to the low, middle or high nutritional media never serves to stimulate the growth of the known strains of Lactobacillus (Table 9-(c)).

Concomitantly, in Tables 9-(a) to (c) it should be noted that the Lactobacillus strains of the invention explained as those which are promoted their growth in the presence of S, N, C-substances include a group of strains which become possible to grow in the presence of said substances.

TABLE 8

| Compounds added to the basic medium | Basic medium | Strains (F.R.I. Nos) | | | | |
|---|---|---|---|---|---|---|
| | | 1946 | 2779 | 2780 | 2781 | 2782 |
| No addition | A | − | − | − | − | − |
| | B | − | − | − | − | − |
| | C | + | + | + | + | + |
| | D | ++ | ++ | ++ | ++ | ++ |
| Acetic acid | A | ⊥ | − | − | ⊥ | − |
| | B | + | − | − | + | − |
| | C | +⊥ | +⊥ | +⊥ | ++ | +⊥ |
| | D | ++ | ++ | ++ | ++ | ++ |

TABLE 8-continued

| Compounds added to the basic medium | Basic medium | Strains (F.R.I. Nos) | | | | |
|---|---|---|---|---|---|---|
| | | 1946 | 2779 | 2780 | 2781 | 2782 |
| Ammonia | A | ⊥ | − | − | ⊥ | − |
| | B | + | − | − | ⊥ | − |
| | C | +⊥ | +⊥ | +⊥ | ++ | + |
| | D | ++ | ++ | ++ | ++ | ++ |
| Propionic acid | A | ⊥ | − | − | ⊥ | − |
| | B | + | − | − | + | − |
| | C | +⊥ | ++ | +⊥ | ++ | +⊥ |
| | D | ++ | ++ | ++ | ++ | ++ |
| $Na_2S.9H_2O$ | A | ⊥ | − | − | ⊥ | − |
| | B | ++ | − | − | + | − |
| | C | ++ | +⊥ | +⊥ | ++ | ++ |
| | D | ++ | ++ | ++ | ++ | ++ |
| Butyric acid | A | ⊥ | − | − | ⊥ | − |
| | B | + | − | − | + | − |
| | C | ++ | ++ | +⊥ | ++ | +⊥ |
| | D | ++ | ++ | ++ | ++ | ++ |
| Scatole | A | − | − | − | ⊥ | − |
| | B | + | − | − | ⊥ | − |
| | C | + | + | +⊥ | +⊥ | + |
| | D | ++ | ++ | ++ | ++ | ++ |
| Excremental juice | A | + | + | + | + | + |
| | B | +⊥ | + | + | + | + |
| | C | ++ | +⊥ | +⊥ | +⊥ | +⊥ |
| | D | ++ | ++ | ++ | ++ | ++ |

Note:
(A): S-W medium
(B): S-W medium (+ Agar)
(C): Peptone 8 g + Glucose 2 g
(D): Peptone 10 g + Meat extract 5 g + NaCl 5 g + Glucose 1 g TABLE 9-(a)

| Basic medium | | Degree of growth of Lactobacillus | | Amount of acetic acid added (g/liter) | Degree of stimulation of Lactobacillus | |
|---|---|---|---|---|---|---|
| | | Known strain | Strain of the invention | | Known strain | Strain of the invention |
| Low nutrition | | − | + | 1 | − | + |
| | | | | 2 | − | +⊥ |
| | | | | 5 | − | ++ |
| | Low | − | + | 1 | − | + |
| | | | | 2 | − | +⊥ |
| | | | | 5 | − | ++ |
| Middle nutrition | Middle | ⊥ | + | 1 | −~⊥ | ⊥ |
| | | | | 2 | ⊥ | + |
| | | | | 5 | + | +⊥ |
| | High | ⊥ | ++ | 1 | ⊥ | − |
| | | | | 2 | ⊥ | ⊥ |
| | | | | 5 | + | + |
| High nutrition | | + | ++ | 1 | ⊥ | − |
| | | | | 2 | + | − |
| | | | | 5 | +⊥ | + |

TABLE 9-(b)

| Basic medium | | Amount of $Na_2S.9H_2O$ added (g/l) | Degree of stimulation of Lactobacillus in the presence of $Na_2S.9H_2O$ | | Amount of ammonia added (g/l) | Degree of stimulation of Lactobacillus in the presence of ammonia | |
|---|---|---|---|---|---|---|---|
| | | | Known strain | Strain of invention | | Known strain | Strain of invention |
| Low nutrition | | 0.1 | − | ⊥ | 0.1 | − | ⊥ |
| | | 1 | − | ⊥ | 1 | − | ⊥ |
| | | 2 | − | −* | 2 | − | ⊥ |
| | Low | 0.1 | − | ⊥ | 0.1 | − | ⊥ |
| | | 1 | − | ⊥ | 1 | − | ⊥ |
| | | 2 | − | −* | 2 | − | ⊥ |
| Middle nutrition | Middle | 0.1 | −* | ⊥ | 0.1 | − | ⊥ |
| | | 1 | −* | + | 1 | −* | ⊥ |
| | | 2 | −* | −* | 2 | −* | ⊥ |
| | High | 0.1 | − | ⊥ | 0.1 | − | − |
| | | 1 | −* | + | 1 | −* | − |
| | | 2 | −* | −* | 2 | −* | − |
| High | | 0.1 | − | − | 0.1 | − | − |

TABLE 9-(b)-continued

| Basic medium | Amount of Na$_2$S . 9H$_2$O added (g/l) | Degree of stimulation of Lactobacillus in the presence of Na$_2$S . 9H$_2$O Known strain | Degree of stimulation of Lactobacillus in the presence of Na$_2$S . 9H$_2$O Strain of invention | Amount of ammonia added (g/l) | Degree of stimulation of Lactobacillus in the presence of ammonia Known strain | Degree of stimulation of Lactobacillus in the presence of ammonia Strain of invention |
|---|---|---|---|---|---|---|
| nutri- | 1 | —* | — | 1 | — | — |
| tion | 2 | —* | —* | 2 | —* | — |

Note: —*: Growth depression

TABLE 9-(c)

| Basic medium | | Amount of compounds added (g/l) Na$_2$S . 9H$_2$O | NH$_3$ | Acetic acid | Degree of stimulation of *lactobacillus* in the presence of S, N, D-substances Known strain | Strain of the invention |
|---|---|---|---|---|---|---|
| Low nutrition | | 0.1 | + 0.1 | + 0.1 | — | ⊥ |
| | | 1 | + 1 | + 1 | — | + |
| | | 2 | + 2 | + 2 | — | —* |
| | Low | 0.1 | + 0.1 | + 0.1 | — | ⊥ |
| | | 1 | + 1 | + 1 | — | + |
| | | 2 | + 2 | + 2 | — | —* |
| Middle nutrition | Middle | 0.1 | + 0.1 | + 0.1 | — | ⊥ |
| | | 1 | + 1 | + 1 | —* | + |
| | | 2 | + 2 | + 2 | —* | —* |
| | High | 0.1 | + 0.1 | + 0.1 | — | ⊥ |
| | | 1 | + 1 | + 1 | —* | ⊥ |
| | | 2 | + 2 | + 2 | —* | —* |
| High nutrition | | 0.1 | + 0.1 | + 0.1 | — | — |
| | | 1 | + 1 | + 1 | —* | — |
| | | 2 | + 2 | + 2 | —* | —* |

The low, middle and high nutritional media shown in Table 9 are each defined as those which are obtained by classifying the nutritional requirements of the known Lactobacillus strains or those of the present invention into three groups, and the middle nutrition into further three groups, while taking into account the biological properties thereof. However these classifications are not equally applicable to the other ordinary bacteria. More specifically, the low nutritional medium shown herein refers to a medium containing (S-W)+vitamines or (S-W)+Casamino acids (vitamine-free) at most. Of course, in the medium, other specific vitamines or amino acids may be used in place of said vitamines or casamino acids; or alternatively a medium not containing both of said ingredients may be used. Namely, the low nutritional medium described herein should be interpreted as referring to all the media between above described and (S-W) medium.

On the other hand, the low nutrition of the middle nutritional medium shown in Table 9 refers to (S-W)+vitamines+sulfur-containing amino acids; and the middle nutrition of the middle nutritional medium refers to (S-W)+vitamines+casamino acids, peptone+sugars, or a medium of almost the same nutritional value thereto. The high nutrition of the middle nutritional medium refers to those which consist of the same ingredients as those of the high nutritional medium but contain only 1/5 to ⅓ nutriments of the latter. In this connection, however, a medium in which some other vitamines and amino acids are added to (S-W)-medium in place of the vitamines and casamino acids used above may also be employed as the middle nutritional medium.

Further, the high nutritional medium stated hereinbefore refers to any media which are, as already disclosed in various scientific reports, especially suitable for proliferation of the known Lactobacillus strains. And such media include not only MRS-medium, but also those which contain amino acids, peptides, nucleic acids, vitamines, minerals, fatty acids or their esters and/or sugars in good nutritional proportions suitable for growth of the known Lactobacillus strains.

Anyway, it should be understood that the Lactobacillus strains of the present invention are not limited to the five strains mentioned above but include any strains which have the same morphological and biological properties as defined hereinbefore, though the therapeutic effects thereof may vary depending on the strains to be used. Additionally, while the antibiotic-productivity of the strains of the invention is important in aiding the therapeutic effects thereof indirectly, it has been ascertained in our experiments that the strains of the invention having no such productivity also show their effects quite satisfactorily.

(g) Some examples of making the present preparation are shown illustratively in the following lines.

(i) A Lactobacillus strain of the present invention was inoculated into a medium (pH 7.4) containing the following ingredients:
  Skim milk
  Yeast extracts
  CaCO$_3$ The medium was cultivated by allowing it to stand at 37° C. for 3 days. Then, the medium was centrifuged under cooling and the collected microbial cells were dried in vacuo, whereby a pharmaceutical Lactobacillus preparation was obtained.

(ii) A Lactobacillus strain of the present invention was inoculated into a medium (pH 7.4) containing the following ingredients:

| | Components of S-W medium: |
|---|---|
| S-W medium* Na$_2$S . 9H$_2$O Acetic acid Propionic acid Butyric acid Yeast extracts Vitamines Amino acids | [ KH$_2$PO$_4$, MgSO$_4$ . 7H$_2$O, NaCl, (NH$_4$)$_2$HPO$_4$, FeSO$_4$ . 7H$_2$O and glucose ] |

The medium was cultivated by allowing it to stand at 37° C. for 3 days. Then, a Lactobacillus preparation was prepared by drying the microbial cells, while keeping them from impaired, until the water content thereof becomes 2%.

The Lactobacillus preparation of the present invention comprises a single or plural strains of the Lactobacillus which are made possible to grow or are promoted their growth by adding one, two, or three substances selected from S-substances, N-substances and C-substances, or a combination thereof to a medium which, in cultivating the known strains of Lactobacillus, does not permit to promote the growth thereof in the presence of C-substances.

Then, the Examples of the present invention are shown in details in the following lines, with a proviso that it will not be limited thereto.

EXAMPLE 1

The present preparation was applied to three patients of acute sinusitis, five patients of chronic sinusitis and two patients of postoperative sinusitis. That is, 20 g of the present preparation (water content: 2%) were dissolved in 400 ml of water, and the nasal sinus of the patients were washed with said solution twice a day for 21 consecutive days. Further, for the two patients who showed strong mucous nasal fluids discharge, the present preparation was used in combination with tetracycline. Based on the subjective symptoms (rhinostenosis, post-nasal discharge, nasal discharge, depression in the sence of smelling, headache), (2) the pathological observation of nasal sinus and nasal mucous membrane (flare of mucous membrane, swelling, amount of nasal discharge, nature of nasal fluids) and (3) direct and X-ray examination, the therapeutic effects of the present preparation was estimated as 4 points (remarkably effective), 2 points (effective), 1 point (slightly effective) and 0 point (ineffective). Table 10 shows the effects of the present preparation at one and 3 weeks after the treatment was started.

TABLE 10

| | | | | (One week after the treatment was started) | | | | | |
|---|---|---|---|---|---|---|---|---|---|
| No. | Initial of Name | Age | Sex | Name of disease | Drug used together | Subjective symptom | Pathological observation | X-ray | Average |
| 1 | M.O. | 10 | ♂ | Acute sinusitis | none | 2 | 1 | 1 | 1.3 |
| 2 | T.M. | 25 | ♀ | Acute sinusitis | none | 2 | 2 | 1 | 1.7 |
| 3 | K.H. | 44 | ♂ | Acute sinusitis | none | 1 | 1 | 1 | 1 |
| 4 | K.A. | 20 | ♀ | Chronic sinusitis | none | 2 | 2 | 2 | 2 |
| 5 | N.N. | 36 | ♀ | Chronic sinusitis | antibiotic | 2 | 1 | 1 | 1.3 |
| 6 | Y.E. | 62 | ♂ | Chronic sinusitis | none | 1 | 1 | 1 | 1 |
| 7 | K.Y. | 51 | ♀ | Chronic sinusitis | none | 1 | 1 | 1 | 1 |
| 8 | Y.M. | 18 | ♀ | Chronic sinusitis | none | 2 | 2 | 2 | 2 |
| 9 | T.T. | 26 | ♂ | Postoperative sinusitis | antibiotic | 1 | 2 | 1 | 1.3 |
| 10 | S.O. | 42 | ♂ | Postoperative sinusitis | none | 2 | 1 | 2 | 1.7 |

| | (Three weeks after the treatment was started) | | | |
|---|---|---|---|---|
| No. | Subjective symptom | Pathological observation | X-ray | Average |
| 1 | | 4 | 2 | 2 | 2.7 |
| 2 | | 4 | 4 | 2 | 3.3 |
| 3 | | 2 | 2 | 2 | 2 |
| 4 | | 4 | 2 | 2 | 2.7 |
| 5 | Same as above | 2 | 2 | 1 | 1.7 |
| 6 | | 2 | 2 | 1 | 1.7 |
| 7 | | 2 | 2 | 2 | 2 |
| 8 | | 2 | 2 | 2 | 2 |
| 9 | | 2 | 4 | 2 | 2.7 |
| 10 | | 4 | 2 | 2 | 2.7 |

As seen in the tables, when the present preparation was used for the ten patients, said preparation was proven to be remarkably effective for the treatment of the sinusitis in one of the patients; effective in six patients; and slightly effective in two patients. Further, in this example, no case was observed in which the present preparation was ineffective in all of the three items of the examination.

EXAMPLE 2

Patients treated: 10 patients of hemorrhoids who were mainly afflicted with pain, swelling or bleeding (16–60 years old).

Methods of Application:
(A) ... the dried cell (water content: 2%) of a Lactobacillus strain which was resistant to tetracycline.

The preparation was administered orally 5 times a day (Dose 3 g per each time).

(B) . . . The same preparation was mixed with a ½-fold volume of an ointment and applied to an affected part 5 times a day.

(C) . . . An ointment of tetracycline was applied to an affected part prior to application of the present preparation.

The tests were first carried out by the following three methods: i.e., (C)+(A), (C)+(B) and (C)+(B).

Judgement as to their effects: Based on the subjective symptoms and the secondary observations such as subjective pain, bleeding, swelling, the degree of hemorrhoidal nodule and a sense of incongruity at the anus, the therapeutic effects was ranked as +4 (remarkably effective), +2 (effective), +1 (slightly effective), 0 (ineffective) and −2 (aggravated).

The therapeutic affects were observed in 7th, 14th, and 21th day. Further, Table 11 shows the results which were carried out according to (A)+(B)+(C) and were estimated in 7th and 21th day after the treatment was started.

TABLE 11

(One week after the treatment was started)

| Name | Subjective pain | Bleeding | Swelling | Degree of hemorrhoidal nodule | Sense of incongruity | Average |
|---|---|---|---|---|---|---|
| Y.T. | 1 | 1 | 1 | 1 | 1 | 1 |
| K.H. | 2 | 2 | 1 | 1 | 1 | 1.4 |
| M.M. | 4 | 4 | 2 | 2 | 2 | 2.8 |
| T.S. | 1 | 1 | 1 | 1 | 1 | 1 |
| T.H. | 1 | 1 | 1 | 1 | 1 | 1 |
| K.M. | 2 | 1 | 1 | 1 | 1 | 1.2 |
| M.O. | 2 | 2 | 2 | 2 | 1 | 1.8 |
| S.S. | 1 | 1 | 1 | 1 | 1 | 1 |
| N.H. | 1 | 2 | 1 | 2 | 1 | 1.4 |
| T.Y. | 1 | 1 | 1 | 1 | 1 | 1 |

The results were characteristic in that there was not observed any cases of "ineffective" and "aggravated".

(Three weeks after the treatment was started)

| Name | Subjective pain | Bleeding | Swelling | Degree of hemorrhoidal nodule | Sense of incongruity | Average |
|---|---|---|---|---|---|---|
| Y.T. | 2 | 2 | 2 | 2 | 2 | 2 |
| K.H. | 2 | 2 | 2 | 2 | 2 | 2 |
| M.M. | 4 | 4 | 4 | 2 | 4 | 3.6 |
| T.S. | 1 | 1 | 1 | 1 | 1 | 1 |
| T.H. | 2 | 2 | 2 | 2 | 2 | 2 |
| K.N. | 2 | 2 | 2 | 2 | 1 | 1.8 |
| M.O. | 4 | 4 | 2 | 2 | 2 | 2.8 |
| S.S. | 2 | 1 | 1 | 1 | 1 | 1.2 |
| N.H. | 2 | 2 | 2 | 2 | 2 | 2 |
| T.Y. | 2 | 1 | 1 | 1 | 1 | 1.2 |

The characteristics of this test results was that there was no case which showed "4" or "0" in all of the five examination items.

EXAMPLE 3

Table 12 shows the result of the clinical tests which were carried out in the field of the dentistry by the use of the present preparation. The tests were carried out by (i) packing it (2% dried cells) directly into the affected part,
(ii) dissolving the present preparation in a physiological saline solution, and then injecting said solution with an injector,
(iii) gargling the throat with an aqueous solution of the present preparation, or
(iv) applying the ointment of the present preparation to the affected part.

The results were indicated as +++ (remarkably effective), ++ (fairly effective), + (effective) and − (ineffective).

TABLE 12

| No. | Name of patient | Sex | Age | Position and symptom | Method of operation | Method of administration | Effects |
|---|---|---|---|---|---|---|---|
| 1 | K.S. | ♀ | 37 | gingival abscess | Extraction of tooth | (i) | ++ |
| 2 | T.A. | ♀ | 25 | gingival abscess | none | (ii) | + |
| 3 | H.O. | ♂ | 46 | alveolar abscess | none | (iv) | +++ |
| 4 | E.M. | ♂ | 22 | alveolar abscess | none | (iv) | ++ |
| 5 | S.I. | ♀ | 19 | periodontitis | Extraction of tooth | (i) | ++ |
| 6 | T.H. | ♂ | 40 | periodontitis | Extraction of tooth | (ii) | + |
| 7 | T.M. | ♀ | 57 | wisdom-tooth's inflammation | Extraction of tooth | (iii) | ++ |
| 8 | S.N. | ♀ | 60 | wisdom-tooth's inflammation | none | (iv) | +++ |
| 9 | M.N. | ♀ | 21 | gingival abscess | none | (iii) | ++ |
| 10 | S.T. | ♀ | 34 | gingival abscess | none | (ii) | ++ |
| 11 | M.K. | ♂ | 30 | gingival abscess | Extraction of tooth | (i) | + |
| 12 | M.N. | ♂ | 27 | pulpitis of tooth | Extraction | (i) | + |

As is clear from the table, the high therapeutic effects were observed in almost all of the patients.

EXAMPLE 4

The present preparation was used for the treatment of the pudendal laceration and the swelling or pain shown after the operation of pudenda. That is, in the tests the ointment of the preparation was applied to the local section several times a day. Further, in the case of heavy laceration, the present preparation was used in combination with antibiotics and protease. The results are shown in Table 13.

TABLE 13

| No. | Name | Age | Child birth | Symptoms | Degree of swelling | Degree of Sewing pain | A* up | T** (g/day) | (times) | Observation |
|---|---|---|---|---|---|---|---|---|---|---|
| 1 | W.M. | 26 | first | pudendal laceration | ++ | ++ | pudendal vagina | 3 | 5 | 2 days later: swelling and pain alleviated; good sewing up |
| 2 | K.K. | 24 | " | pudendal laceration | + | " | pudendal vagina | " | " | 2 days later: swelling and pain alleviated; good sewing up |
| 3 | M.A. | 30 | " | pudendal laceration | ++ | " | pudendal vagina | " | 4 | 2 days later: swelling alleviated. 4 days later: pain alleviated; good sewing up |
| 4 | J.S. | 21 | " | pudendal laceration | ++ | " | pudendal vagina | " | 5 | 2 days later: swelling alleviated. 4 days later: pain alleviated; good sewing up |
| 5 | M.M. | 29 | " | incision of pudenda | ++ | " | pudendal vagina | 3 (antibiotic and protease) | 4 | 2 days later, swelling alleviated. 4 days later: pain alleviated; good sewing up |

Note:
A*:Amount applied (g/day)
T**:Number of times applied (times/day)

The treatment was effective in all of the five patients. They convalesced satisfactorily.

Despite the findings of strong antibiotics, the above-mentioned diseases still belong to a group of diseases which have been recognized to be difficult to cure in the present day's medical science. Accordingly, it will be concluded that the theory of the present invention are applicable almost equally to other infectious diseases which are induced based on the substantially same mechanisms as the above-mentioned ones.

EXAMPLE 5

After the operation of appendicitis, the present preparation was used for the removal of pathogenic bacteria, fibrin produced in the local section, died tissues, nasal fluids and so forth, or for the treatment of pathogenic bacteria-induced gastritis and enteritis. Said preparation was administered orally and in almost all cases in combination with antibiotics. In comparison with untreated patients, the results were indicated as +++ (remarkably effective, ++ (fairly effective), + (effective) and − (ineffective). Concomitantly, the Lactobacillus strain used in this experiments was the one which is resistant to the antibiotics used, and in the case of adult patients the present preparation (the fresh cultivation broth) was administered 8 times a day at the dose of 3 ml/kg of body weight/each time.

TABLE 14

| No. | Sex | Age | Name of operation | Remarks | Conditions after the operation | Effects |
|---|---|---|---|---|---|---|
| 1 | ♂ | 38 | removal of appendix | | good | ++ |
| 2 | ♂ | 57 | removal of appendix | | good | + |
| 3 | ♀ | 40 | removal of appendix | | good | + |
| 4 | ♀ | 29 | removal of appendix | | good | ++ |
| 5 | ♂ | 35 | enteritis | bibrio | good | ++ |
| 6 | ♀ | 32 | enteritis | bibrio | good | + |
| 7 | ♂ | 18 | enteritis | salmonella | good | + |
| 8 | ♂ | 24 | enteritis | salmonella | good | +++ |

Table 14 clearly shows that all the patients convalesced satisfactorily and the present preparation had a high therapeutic effects. Especially, although it sometimes happened in the past cases in appendicitis that the wound could not be sewn up well or the surgical operation had to be repeated because of distribution of bacteria around the affected part or the insufficient inhibitory effects of antibiotics against bacteria, such accidents were not observed during the experiments shown in the tables or other various experiments connected therewith.

What we claim is:
1. A process for treating a patient having infection or infectious disease which comprises administering locally to said patient, in an amount effective to treat said infection or infectious disease, at least one microorganism strain which is similar to conventional Lactobacil- lus strains in its morphological properties, but different from known strains of Lactobacillus in its nutritional requirements, said strain of microorganism being able to grow in or the growth of which is promoted by a culture medium comprising (1) a low nutrition culture medium wherein conventional Lactobacillus is unable to grow, and (2) at least one substance selected from the group consisting of (a) Na$_2$S, (b) NH$_3$, (c) lower fatty acids and (d) mixtures thereof, said lower fatty acids not promoting the growth of conventional Lactobacillus when added to said low nutrition culture medium, said at least one strain being selected from the group consisting of microorganism FRI strain No. 1946, microorganism FRI strain No. 2779, microorganism FRI strain No. 2780, microorganism FRI strain No. 2781 and microorganism FRI strain No. 2782.

2. The process of claim 1 wherein said Lactobacillus strain is administered with an antibiotic.

3. The process of claim 1 wherein said Lactobacillus strain is bile-resistant.

4. The process of claim 1 wherein said Lactobacillus strain can produce an antibiotic.

5. The process of claim 1 wherein said Lactobacillus strain has bacterial resistance.

6. A process for treating a patient having sinusitis which comprises washing the nasal sinus of said patient with a liquid pharmaceutical preparation comprising (1) in an amount effective to treat sinusitis, at least one microorganism strain which is similar to conventional Lactobacillus strains in its morphological properties, but different from known strains of Lactobacillus in its nutritional requirements, said strain of microorganism being able to grow in or the growth of which is promoted by a culture medium comprising (1) a low nutrition culture medium wherein conventional Lactobacillus is unable to grown, and (2) at least one substance selected from the group consisting of (a) Na$_2$S, (b), NH$_3$, (c) lower fatty acids and (d) mixtures thereof, said lower fatty acids not promoting the growth of conventional Lactobacillus when added to said low nutrition culture medium, said at least one strain being selected from the group consisting of microorganism FRI strain No. 1946, microorganism FRI strain No. 2779, microorganism FRI strain No. 2780, microorganism FRI strain No. 2781 and microorganism FRI strain No. 2782 and (2) a conventional carrier.

7. The process of claim 6 wherein the pharmaceutical preparation is a water solution and contains an antibiotic.

8. A process for treating a patient having hemorrhoids which comprises applying to affected areas of said patient a pharmaceutical preparation comprising (1) in an amount effective to treat hemorrhoids, at least one microorganism strain which is similar to conventional Lactobacillus strains in its morphological properties, but different from known strains of Lactobacillus in its nutritional requirements, said strain of microorganism being able to grow in or the growth of which is promoted by a culture medium comprising (1) a low nutrition culture medium wherein conventional Lactobacillus is unable to grow, and (2) at least one substance selected from the group consisting of (a) Na$_2$S, (b) NH$_3$, (c) lower fatty acids and (d) mixtures thereof, said lower fatty acids not promoting the growth of conventional Lactobacillus when added to said lower nutrition culture medium, said at least one strain being selected from the group consisting of microorganism FRI strain No. 1946, microorganism FRI strain No. 2779, microorganism FRI strain No. 2780, microorganism FRI strain No. 2781 and microorganism FRI strain No. 2782, and (2) a conventional carrier in the form of an ointment and also applying to said affected areas an antibiotic ointment suitable for treating hemorrhoids, said Lactobacillus strain being resistant to said antibiotic.

9. The process of claim 8, wherein a pharmaceutical preparation comprising (1) in an amount effective to treat hemorrhoids, at least one microorganism strain which is similar to conventional Lactobacillus strains in its morphological properties, but different from known strains of Lactobacillus in its nutritional requirements, said strain of microorganism being able to grow in or the growth of which is promoted by a culture medium comprising (1) a low nutrition culture medium wherein conventional Lactobacillus is unable to grow, and (2) at least one substrate selected from the group consisting of (a) Na$_2$S, (b) NH$_3$, (c) lower fatty acids and (d) mixtures thereof, said lower fatty acids not promoting the growth of conventional Lactobacillus when added to said low nutrition culture medium, said at least one strain being selected from the group consisting of microorganism FRI strain No. 1946, microorganism FRI strain No. 2779, microorganism FRI strain No. 2780, microorganism FRI strain No. 2781 and microorganism FRI strain No. 2782, and (2) a conventional carrier is also administered orally to said patient.

10. The process of claim 8 wherein said antibiotic is Tetracycline.

11. The process of claim 9 wherein said antibiotic is tetracycline.

12. A process for treating a patient having gingival abscess, alveolar abscess, periodontitis, tooth inflammation or pulpitis in dentistry which comprises applying locally to the affected parts of said patient a pharmaceutical preparation comprising (1) in an amount effective to treat said gingival abscess, alveolar abscess, periodontitis, tooth inflammation or pulpitis, at least one microorganism strain which is similar to conventional Lactobacillus strains in its morphological properties, but different from known strains of Lactobacillus in its nutritional requirements, said strain of microorganism being able to grow in or the growth of which is promoted by a culture medium comprising (1) a low nutrition culture medium wherein conventional Lactobacillus is unable to grow, and (2) at least one substance selected from the group consisting of (a) Na$_2$S, (b) NH$_3$, (c) lower fatty acids and (d) mixtures thereof, said lower fatty acids not promoting the growth of conventional Lactobacillus when added to said low nutrition culture medium, said at least one strain being selected from the group consisting of microorganism FRI strain No. 1946, microorganism FRI strain No. 2779, microorganism FRI strain No. 2780, microorganism FRI strain No. 2781 and microorganism FRI strain No. 2782, and (2) a conventional carrier.

13. The process of claim 12 wherein said preparation is in the form of a pack of dry cells, a solution or an ointment.

14. A process for treating a patient having pudendal laceration which comprises applying locally to affected areas of said patient a pharmaceutical preparation comprising (1) in an amount effective to treat pudendal laceration, at least one microorganism strain which is similar to conventional Lactobacillus strains in its morphological properties, but different from known strains of Lactobacillus in its nutritional requirements, said strain of microorganism being able to grow in or the growth of which is promoted by a culture medium comprising (1) a low nutrition culture medium wherein conventional Lactobacillus is unable to grow, and (2) at least one substance selected from the group consisting of (a) Na₂S, (b) NH₃, (c) lower fatty acids and (d) mixtures thereof, said lower fatty acids not promoting the growth of conventional Lactobacillus when added to said low nutrition culture medium, said at least one strain being selected from the group consisting of microorganism FRI strain No. 1946, microorganism FRI strain No. 2779, microorganism FRI strain No. 2780, microorganism FRI strain No. 2781 and microorganism FRI strain No. 2782, and (2) a conventional carrier.

15. The process of claim 14 wherein said pharmaceutical preparation also includes at least one of an antibiotic and a protease, said Lactobacillus strain being resistant to said antibiotic.

16. A process for treating a patient having sinusitis or colpitis which comprises administering by local, nasal or vaginal administration, in an amount effective to treat said sinusitis or colpitis, at least one microorganism strain which is similar to conventional Lactobacillus strains in its morphological properties, but different from known strains of Lactobacillus in its nutritional requirements, said strain of microorganism being able to grow in or the growth of which is promoted by a culture medium comprising (1) a low nutrition culture medium wherein conventional Lactobacillus is unable to grow, and (2) at least one substance selected from the group consisting of (a) Na₂S, (b) NH₃, (c) lower fatty acids and (d) mixtures thereof, said lower fatty acids not promoting the growth of conventional Lactobacillus when added to said low nutrition culture medium, said at least one strain being selected from the group consisting of microorganism FRI strain No. 1946, microorganism FRI strain No. 2779, microorganism FRI strain No. 2780, microorganism FRI strain No. 2781 and microorganism FRI strain No. 2782.

17. A process for treating a patient having inflammation caused by infectious disease which comprises administering locally to said patient, in an amount effective to treat said inflammation, at least one microorganism strain which is similar to conventional Lactobacillus strains in its morphological properties, but different from known strains of Lactobacillus in its nutritional requirements, said strain of microorganism being able to grow in or the growth of which is promoted by a culture medium comprising (1) a low nutrition culture medium wherein conventional Lactobacillus is unable to grow, and (2) at least one substance selected from the group consisting of (a) Na₂S, (b) NH₃, (c) lower fatty acids and (d) mixtures thereof, said lower fatty acids not promoting the growth of conventional Lactobacillus when added to said low nutrition culture medium, said at least one strain being selected from the group consisting of microorganism FRI strain No. 1946, microorganism FRI strain No. 2779, microorganism FRI strain No. 2780, microorganism FRI strain No. 2781 and microorganism FRI strain No. 2782.

18. The process of claim 1 wherein said at least one strain of Lactabacillus can grow in or the growth of which is promoted by a low nutrition conventional Lactobacillus culture medium to which there is added each of a substance selected from the group consisting of (a) an odoriferous S-substance, (b) an odoriferous N-substance, and (c) a C-substance selected from the group consisting of lower fatty acids and mixtures thereof, said C-substance not promoting the growth of conventional Lactobacillus when added to said low nutrition culture medium.

19. The process of claim 18 wherein said Lactobacillus strain is administered with an antibiotic.

20. The process of claim 18 wherein said Lactobacillus strain is bile-resistant.

21. The process of claim 18 wherein said Lactobacillus strain can produce an antibiotic.

22. The process of claim 18 wherein said Lactobacillus strain has bacterial resistance.

23. The process of claim 6 wherein said at least one strain of Lactobacillus can grow in or the growth of which is promoted by a low nutrition conventional Lactobacillus culture medium to which there is added each of a substance selected from the group consisting of (a) an odoriferous S-substance, (b) an odoriferous N-substance, and (c) a C-substance selected from the group consisting of lower fatty acids and mixtures thereof, said C-substance not promoting the growth of conventional Lactobacillus when added to said low nutrition culture medium.

24. The process of claim 23 wherein the pharmaceutical preparation is a water solution and contains an antibiotic.

25. The process of claim 8 wherein said at least one strain of Lactobacillus can grow in or the growth of which is promoted by a low nutrition conventional Lactobacillus culture medium to which there is added each of a substance selected from the group consisting of (a) an odoriferous S-substance, (b) an odoriferous N-substance, and (c) a C-substance selected from the group consisting of lower fatty acids and mixtures thereof, said C-substance not promoting the growth of conventional Lactobacillus when added to said low nutrition culture medium.

26. The process of claim 9 wherein said at least one strain of Lactobacillus can grow in or the growth of which is promoted by a low nutrition conventional Lactobacillus culture medium to which there is added each of a substance selected from the group consisting of (a) an odoriferous S-substance, (b) an odoriferous N-substance, and (c) a C-substance selected from the group consisting of lower fatty acids and mixtures thereof, said C-substance not promoting the growth of conventional Lactobacillus when added to said low nutrition culture medium.

27. The process of claim 25 wherein said antibiotic is Tetracycline.

28. The process of claim 26 wherein said antibiotic is Tetracycline.

29. The process of claim 12 wherein said at least one strain of Lactobacillus can grow in or the growth of which is promoted by a low nutrition conventional Lactobacillus culture medium to which there is added each of a substance selected from the group consisting of (a) an odoriferous S-substance, (b) an odoriferous N-substance, and (c) a C-substance selected from the group consisting of lower fatty acids and mixtures thereof, said C-substance not promoting the growth of conventional Lactobacillus when added to said low nutrition culture medium.

30. The process of claim 29 wherein said preparation is in the form of a pack of dry cells, a solution or an ointment.

31. The process of claim 15 wherein said at least one strain of Lactobacillus can grow in or the growth of which is promoted by a low nutrition conventional Lactobacillus culture medium to which there is added each of a substance selected from the group consisting of (a) an odoriferous S-substance, (b) an odoriferous N-substance, and (c) a C-substance selected from the group consisting of lower fatty acids and mixtures thereof, said C-substance not promoting the growth of conventional Lactobacillus when added to said low nutrition culture medium.

32. The process of claim 31 wherein said pharmaceutical preparation also includes at least one of an antibiotic and a protease, said Lactobacillus strain being resistant to said antibiotic.

33. The process of claim 32 wherein said pharmaceutical preparation is in the form of an ointment.

34. The process of claim 17 wherein said Lactobacillus strain is administered with an antibiotic.

35. The process of claim 17 wherein said Lactobacillus strain is bile-resistant.

36. The process of claim 17 wherein said Lactobacillus strain can produce an antibiotic.

37. The process of claim 17 wherein said Lactobacillus strain has bacterial resistance.

38. The process of claim 17 wherein said at least one strain of Lactobacillus can grow in or the growth of which is promoted by a low nutrition conventional Lactobacillus culture medium to which there is added each of a substance selected from the group consisting of (a) an odoriferous S-substance, (b) an odoriferous N-substance, and (c) a C-substance selected from the group consisting of lower fatty acids and mixtures thereof, said C-substance not promoting the growth of conventional Lactobacillus when added to said low nutrition culture medium.

39. The process of claim 38 wherein said Lactobacillus strain is administered with an antibiotic.

40. The process of claim 38 wherein said Lactobacillus strain is bile-resistant.

41. The process of claim 38 wherein said Lactobacillus strain can produce an antibiotic.

42. The process of claim 38 wherein said Lactobacillus strain has bacterial resistance.

43. The process of claim 15 wherein said pharmaceutical preparation is in the form of an ointment.

* * * * *